United States Patent [19]

Narula et al.

[11] Patent Number: 5,066,641
[45] Date of Patent: Nov. 19, 1991

[54] 3,5,5-TRIMETHYLHEXANAL OXIME AND ORGANOLEPTIC USES THEREOF

[75] Inventors: Anubhav P. S. Narula, Hazlet; John J. De Virgilio, Freehold, both of N.J.; Jan T. Van Elst, Et Hilversum, Netherlands

[73] Assignee: International Flavors & Fragrances Inc., New York, N.Y.

[21] Appl. No.: 588,844

[22] Filed: Sep. 27, 1990

[51] Int. Cl.$^5$ .............................................. A61K 7/46
[52] U.S. Cl. ...................... 512/25; 564/268; 252/174.11
[58] Field of Search ..................... 512/25, 27; 564/268

[56] References Cited

U.S. PATENT DOCUMENTS

| | | | |
|---|---|---|---|
| 3,637,533 | 1/1972 | Dahill | 252/522 |
| 3,745,213 | 7/1973 | Nysted | 512/4 |
| 4,017,634 | 4/1977 | Lam et al. | 424/300 |
| 4,544,714 | 10/1985 | Ochsner | 252/522 |
| 4,758,548 | 7/1988 | Granlick et al. | 512/25 |
| 4,863,631 | 9/1989 | Sprecker et al. | 252/174.11 |

FOREIGN PATENT DOCUMENTS 2723636  12/1978  Fed. Rep. of Germany ........ 512/27

*Primary Examiner*—James H. Reamer
*Attorney, Agent, or Firm*—Arthur L. Liberman

[57] ABSTRACT

Described is 3,5,5-trimethylhexanal oxime defined according to the structure:

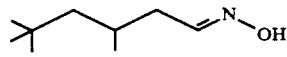

and organoleptic uses thereof in augmenting or enhancing the aroma of perfume compositions, colognes and perfumed articles including but not limited to solid or liquid anionic, cathionic, nonionic and zwitterionic detergents, perfume polymers, fabric softener compositions, fabic softener articles, cosmetic powders and hair preparations.

5 Claims, 4 Drawing Sheets

GLC PROFILE FOR EXAMPLE I.

FIG. 2 NMR SPECTRUM FOR EXAMPLE I.

3,5,5-TRIMETHYLHEXANAL OXIME AND ORGANOLEPTIC USES THEREOF

BACKGROUND OF THE INVENTION

The present invention relates to the compound 3,5,5-trimethylhexanal oxime and uses thereof to alter, modify or enhance the aroma of consumable materials.

There has been considerable work performed relating to substances which can be used to impart (modify, augment or enhance) fragrances too (or in) various consumable materials. These substances are used to diminish the use of natural materials, some of which may be in short supply and to provide more uniform properties in the finished product.

Long-lasting and substantive green, vetivert, woody, earthy, orris, minty, camphoraceous, cassis and grapefruit aromas with minty, camphoraceous, green, herbaceous, vetivert and galbanum topnotes are highly desirable in several types of perfume compositions, perfumed articles and colognes.

The use of oximes is well known in perfumery. Furthermore, the use of oximes is known for their value as intermediates in preparing other compounds such as nitriles.

U.S. Pat. No. 4,863,631 issued on Sept. 5, 1989 (Sprecker, et al) discloses the genus of compounds having the structure:

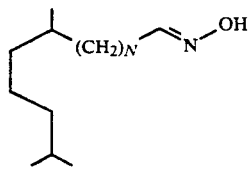

wherein N is 0 or 1 as an intermediate in producing nitriles, which nitriles are useful as perfumery ingredients.

However, U.S. Pat. No. 3,637,533 issued on Jan. 25, 1972 (Dahill) discloses the use of 3,7-dimethyloctanal oxime having the structure:

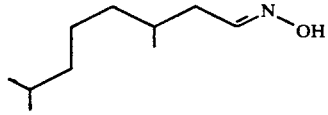

for use in perfumery at Example VI, column 5 and Example XXIII, column 12. Furthermore, the Dahill reference claims a perfume-containing composition comprising an olfactory effective amount of an oxime of a branched chain ethylenic unsaturated hydrocarbyl aldehyde . . . having from 7-10 carbon atoms.

U.S. Pat. No. 4,017,634 issued on Apr. 12, 1977 (Lam, et al.) discloses as a chemical intermediate the compound having the structure:

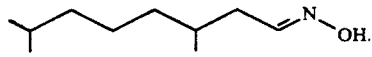

Nothing of the prior art, however, discloses the 3,5,5-trimethylhexanal oxime having unexpected, unobvious, and advantageous organoleptic properties.

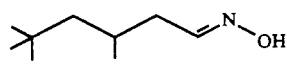

(Conditions: SE-30 column programmed at 220° C. isothermal).

Figure 2:
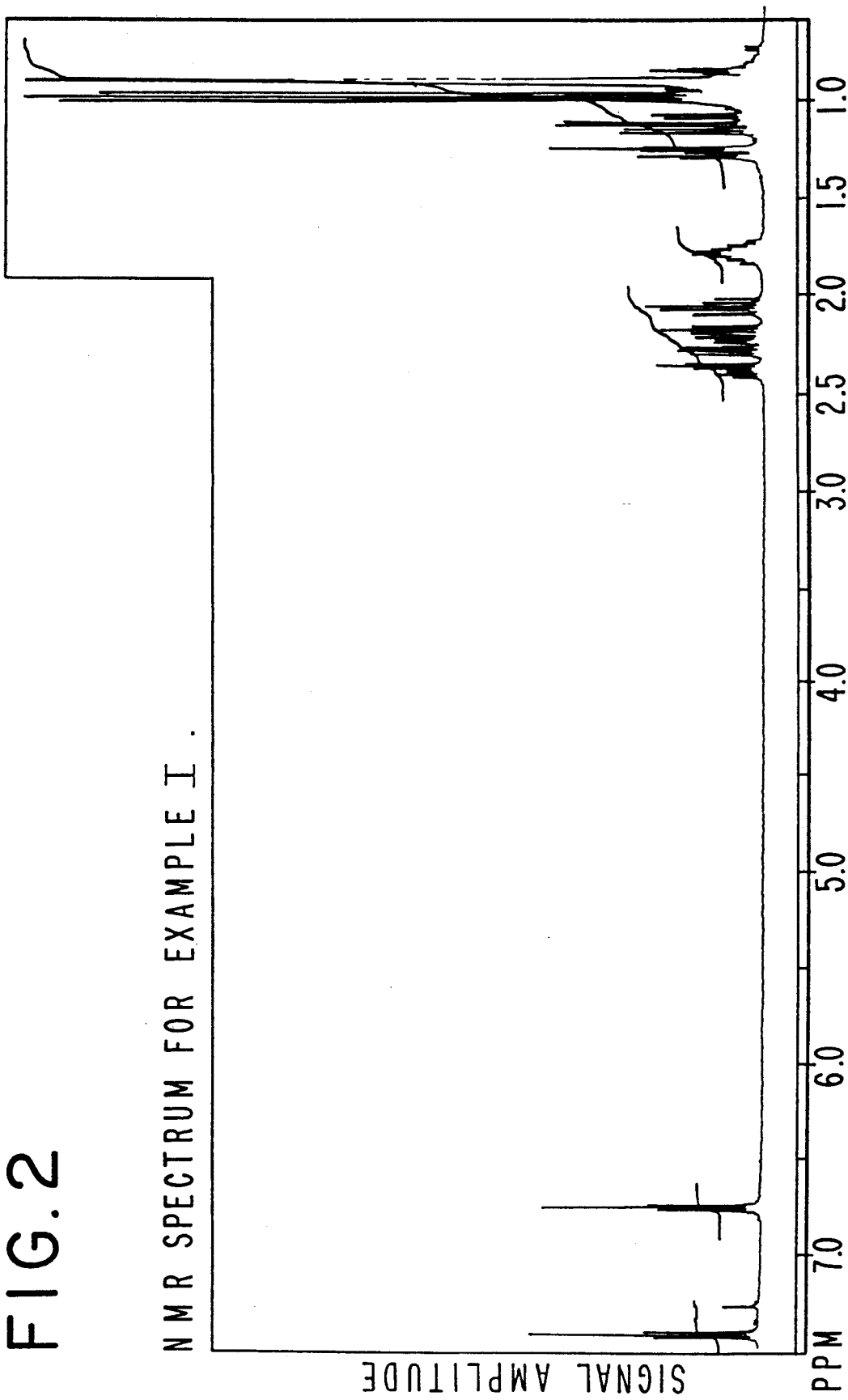

FIG. 2 is the NMR spectrum for the compound having the structure:

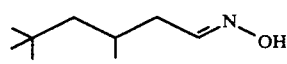

produced according to Example I.

Figure 3:
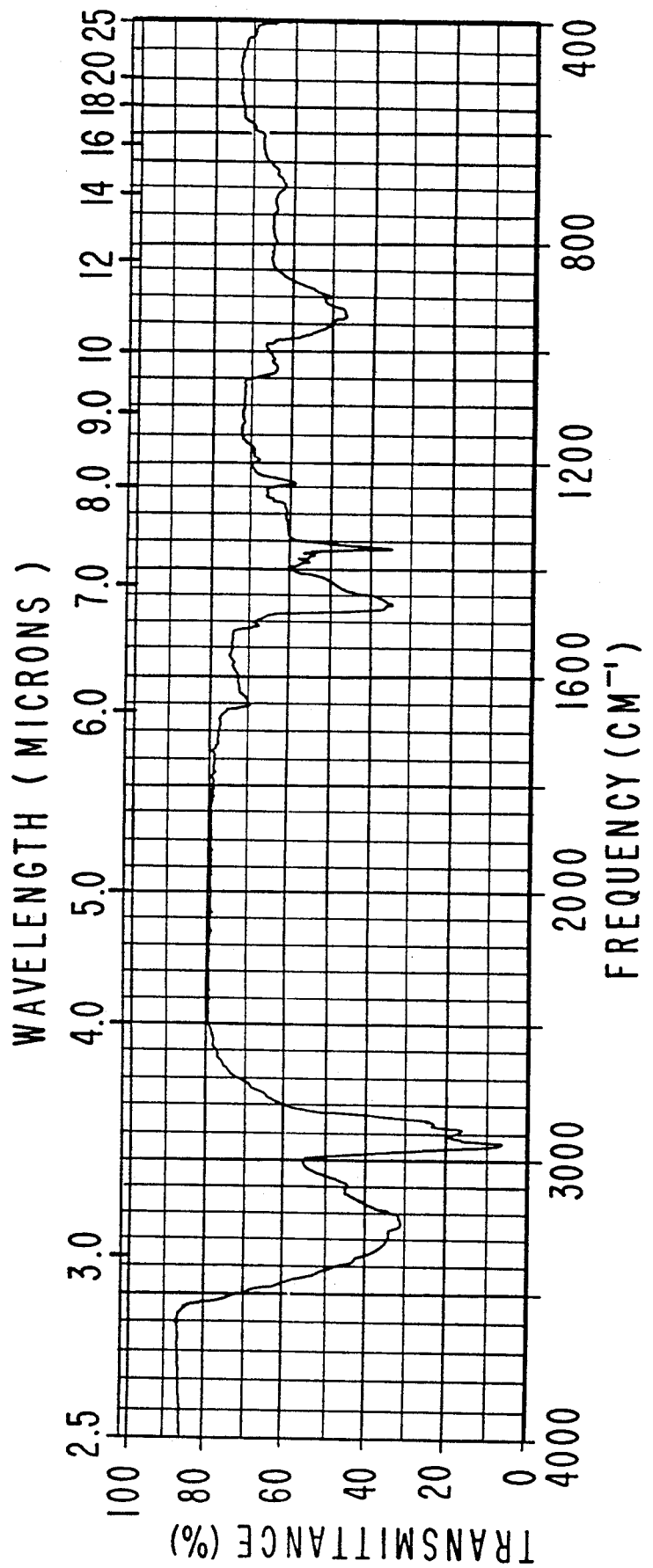

FIG. 3 is the infra-red spectrum for the compound having the structure:

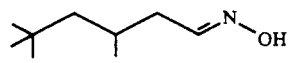

produced according to Example I.

Figures 4, 5:
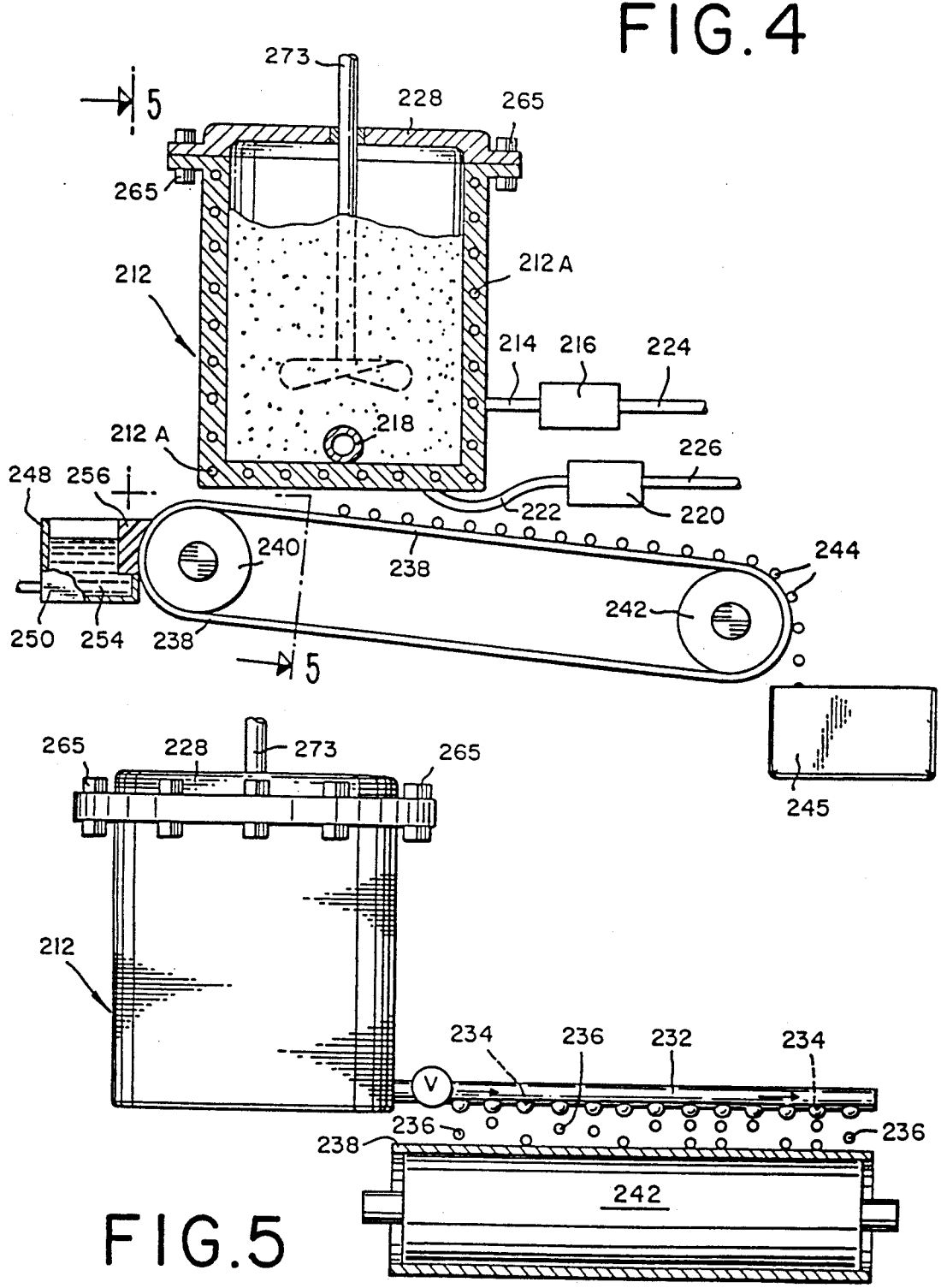

FIG. 4 represents a cutaway side elevation view of apparatus used in forming perfume polymers which contain embedded therein the 3,5,5-trimethylhexanal oxime of our invention.

FIG. 5 is a front view of the apparatus of FIG. IV looking in the direction of the arrows.

DETAILED DESCRIPTION OF THE DRAWINGS

Referring to FIGS. IV and V, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acentat and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. IV and V, in particular, the apparatus used in producing such elements comprises a device for forming the polymer containing the perfume, e.g. polyethylene or polyethylene-polyvinyl acetate or mixtures thereof or polypropylene, which comprises a vat or container 212 into which the polymer taken alone or in admixture with other copolymers and the perfuming substance which is at least the 3,5,5-trimethylhexanal oxime of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostate or control 216 is operated to maintain the temperature inside the container 212 such that the polymer in the container will be maintained in the molten or liquid state. It has been found advantageous to employe polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume compostion or perfume material which contains at least the 3,5,5-trimethylhexanal oxime of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with at least the 3,5,5-trimethylhexanal oxime of our invention or mixture of 3,5,5-trimethylhexanal oxime with other perfumery materials (optionally), will continuously drop or drip through the orifices 234 downwardly from the conduit 232. During this time, the temperature of the polymer intimately admixed with the perfumery substance in the container 212 is accurately controlled so that a temperature in the range of from about 240° C.–250° C. for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains the 3,5,5-trimethylhexanal oxime of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of conveyor 238 into a container 250 which is advantageously filled with water or some other suitable cooling liquid in order to insure the rapid cooling of each of the pellets 244. The pellets 244 are then collected from the container 250 and utilized for the formation of functional products, e.g., garbage bags and the like.

THE INVENTION

The invention provides 3,5,5-trime hylhexanal oxime having the structure:

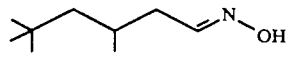

The 3,5,5,-trimethylhexanal oxime of our invention produced according to the process of our invention is capable of augmenting or enhancing green, vetivert, woody, earthy, orris, minty, camphoraceous, cassis and grapefruit aromas with minty, camphoraceous, green, herbaceous, vetivert and galbanum topnotes in perfume compositions, colognes and perfumed articles including soaps, anionic, cationic, nonionic and zwitterionic detergents, fabric softener articles and perfumed articles.

In carrying out the process for preparing the 3,5,5-trimethylhexanal oxime of our invention, the aldehyde having the structure:

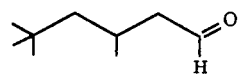

is reacted with a hydroxyl amine salt having the structure:

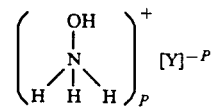

wherein Y represents an anion such as sulfate, chloride or bromide and P is 1 or 2 followed by reaction with base to form the oxime which is the 3,5,5-trimethylhexanal oxime of our invention, having the structure.

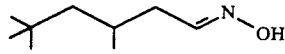

In carrying out the reaction of the compound having the structure:

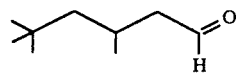

with the compound having the structure:

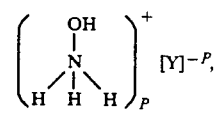

this reaction is carried out at 0°–40° C. at atmospheric pressure. The reaction is a two stage reaction with the first stage being the reaction of the aldehyde having the structure:

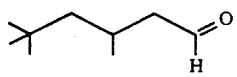

with a hydroxyl amine salt having the structure:

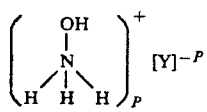

(e.g. hydroxylamine hydrochloride or hydroxylamine sulfate). The second stage of the reaction is reaction with base with or without inert solvent. The base can be sodium hydroxide or calcium hydroxide.

The 3,5,5-trimethylhexanal oxime of our invention and one or more auxiliary perfume ingredients, including, for example, hydrocarbons, alcohols, ketones, aldeydes, nitriles, esters, lactones, ethers, synthetic essential oils and natural essential oils may be admixed so that the combined odors of the individual components produce a pleasant and desired fragrance, particularly and preferably in the green and woody fragrances.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the overall sensory effect of the perfume composition will be at least the sum total of the effects of each of the ingredients. Thus, the 3,5,5-trimethylhexanal oxime of our invention can be used to alter, modify or enhance the aroma characteristics of a perfume composition, for example, by utilizing or moderating the olfactory reaction contributed by another ingredient in the composition.

The amount of the 3,5,5-trimethylhexanal oxime which will be effective in perfume compositions as well as in perfumed articles and colognes depends upon many factors, including the other ingredients, their amounts and the effects which are desired. It has been found that perfume compositions containing as little as 0.05% of the 3,5,5-trimethylhexanal oxime of our invention or even less (e.g., 0.02%) can be used to impart green, vetivert, woody, earthy, orris, minty, camphoraceous, cassis and grapefruit aroma nuances with minty, camphoraceous, green, herbaceous, vetivert and galbanum topnotes to soaps, cosmetics, detergents (including anionic, cationic, nonionic and zwitterionic solid or liquid detergents). The amount employed can range up to 70% of the fragrance components and will depend upon considerations of cost, nature of the end product, the effect desired on the finished product and the particular fragrance sought.

The 3,5,5-trimethylhexanal oxime of our invention is useful (taken alone or together with other ingredients in perfume compositions) in detergents and soaps, space odorants and deodorants, perfumes, colognes, toilet waters, bath preparations such as lacquers, brilliantines, pomades and shampoos; cosmetic preparations, such as creams, deodorants, hand lotions and sun screens; powders such as talcs, dusting powders, face powders and the like. As little as 0.25% of the 3,5,5-trimethylhexanal oxime of our invention will suffice to impart an intense and substantive green, vetivert, woody, earthy, orris, minty, camphoraceous, cassis and grapefruit aroma profile with minty, camphoraceous, green, herbaceous, vetivert and galbanum topnotes to floral and woody perfume formulations. Generally, no more than 5% of the 3,5,5-trimethylhexanal oxime of our invention based on the ultimate end product is required to be used "as-is" or in the perfume composition.

Furthermore, as little as 0.25% of the 3,5,5-trimethylhexanal oxime of our invention will suffice to impart such aroma to perfumed articles per se, whether in the presence of other perfume materials or whether used by itself. Thus, the range of use of the 3,5,5-trimethylhexanal oxime of our invention in perfumed articles may vary from about 0.25% up to about 5% by weight based on the total weight of the perfumed article.

In addition, the perfume composition or fragrance composition of our invention can contain a vehicle, or carrier for the 3,5,5-trimethylhexanal oxime of our invention. The vehicle can be a liquid such as a non-toxic alcohol, e.g. ethanol, a non-toxic glycol, e.g. propylene glycol or the like. The carrier can also be an absorbent solid, such as a gum (e.g., gum arabic), or components for encapsulating the composition by mean of coacervation (such as gelatin).

It will thus be apparent that the 3,5,5-trimethylhexanal oxime of our invention can be utilized to alter, modify or enhance aroma of perfume compositions, colognes and perfumed articles.

The following Example I serves to illustrate a process for producing the 3,5,5-trimethylhexanal oxime of our invention. Examples following Example I in general serve to illustrate organoleptic utilities of the 3,5,5-trimethylhexanal oxime of our invention. All parts and percentages given herewith are by weight unless otherwise specified.

EXAMPLE I

PREPARATION OF 3,5,5-TRIMETHYLHEXANAL OXIME

Reaction:

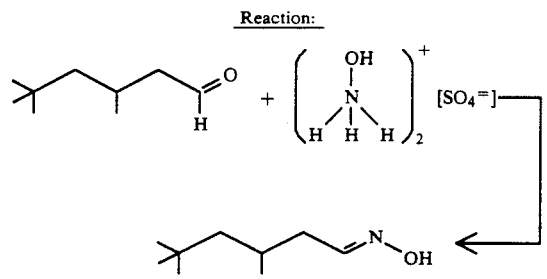

Into a 3 liter reaction flask equipped with stirrer, thermometer, reflux condenser, heating mantle and cooling bath is placed 415 grams (2.5 moles) of hydroxyl amine sulfate and 1600 ml water. The resulting mixture is stirred until homogeneous.

The temperature of the resulting mixture is cooled to 10° C. Rapidly over a period of 5 minutes, 500 grams (3.5 moles) of the compound having the structure:

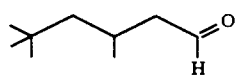

is added to the reaction mass.

Over a period of 1 hour while maintaining the reaction temperature at 55°-57° C., 460 grams (5.75 moles) of sodium hydroxide are added to the reaction mass.

The reaction mass now exists in two phases; an organic phase and an inorganic phase. The organic phase is separated from the inorganic phase. The organic phase is washed with four 1800 ml portions of saturated sodium chloride solution.

The resulting product is then rushed over to yield 473 grams of product (86% yield). The resulting product is then fractionally distilled on 1"×12" Goodloe column yielding the following fractions:

| Fraction No. | Vapor Temp. (°C.) | Liquid Temp. (°C.) | Vaccum mm/Hg | Weighted Fraction |
|---|---|---|---|---|
| 1 | 80 | 91/ | 2.03 | 25 |
| 2 | 93 | 98 | 5.80 | 15 |
| 3 | 93 | 99 | 5.76 | 23 |
| 4 | 93 | 98 | 5.73 | 32 |
| 5 | 93 | 98 | 5.73 | 35 |
| 6 | 93 | 98 | 5.73 | 39 |
| 7 | 97 | 101 | 5.65 | 40 |
| 8 | 93 | 100 | 5.70 | 37 |
| 9 | 93 | 99 | 5.65 | 44 |
| 10 | 94 | 100 | 5.65 | 35 |
| 11 | 94 | 101 | 5.60 | 35 |
| 12 | 94 | 102 | 5.60 | 28 |
| 13 | 94 | 117 | 5.54 | 13 |
| 14 | 94 | 180 | 5.58 | 6 |
| 15 | 94 | 210 | 5.76 | 2 |

Figure 1:
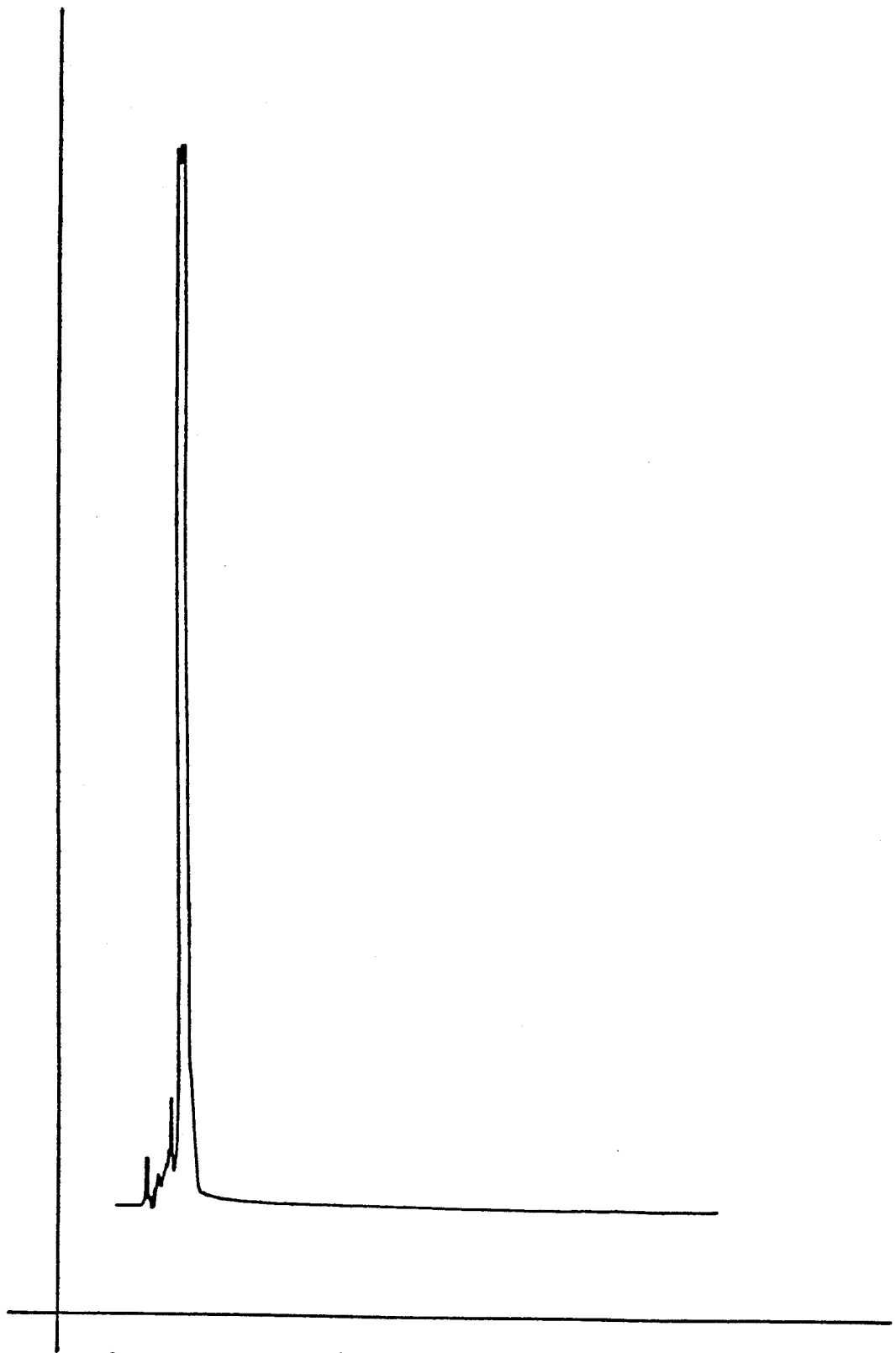
FIG. 1 is the GLC profile for the reaction product of Example I containing the compound having the structure.

FIG. 1 is the GLC profile of the reaction product containing the compound having the structure:

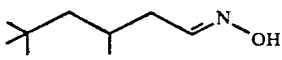

FIG. 2 is the NMR spectrum for the compound having the structure:

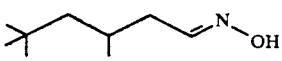

FIG. 3 is the infra-red spectrum of the compound having the structure:

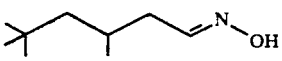

The resulting compound has a green, vetivert, woody, earthy, orris, minty, camphoraceous, cassis and grapefruit aroma profile with minty, camphoraceous, green, herbaceous, vetivert and galbanum topnotes.

EXAMPLE II

The following Chypre formulation is prepared:

| Ingredients | Parts by Weight |
|---|---|
| Musk ambrette | 40 |
| Musk ketone | 60 |
| Coumarin | 30 |
| Oil of bergamot | 150 |
| Oil of lemon | 100 |
| Methyl ionone | 50 |
| Hexyl cinnamic aldehyde | 100 |
| Hydroxycitronellal | 100 |
| Oil of lavender | 50 |
| Texas cedarwood oil | 85 |
| Virginia cedarwood oil | 30 |
| Oil of sandalwood (East Indies) | 40 |
| Isoeugenol | 20 |
| Eugenol | 10 |
| Benzyl acetate | 30 |
| β-phenyl ethyl alcohol | 40 |
| @-phenyl ethyl alcohol | 30 |
| Oakmoss absolute | 30 |
| Vetiver Oil Venezuela | 25 |
| The compound having the structure: 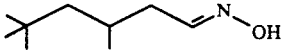 | 62 |

The compound having the structure:

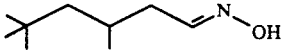

imparts to this Chypre formulation green, vetivert, woody, earthy, orris, minty, camphoraceous, cassis and grapefruit undertones with minty, camphoraceous, green, herbaceous, vetivert and galbanum topnotes. Accordingly, the formulation can be described from a perfumery standpoint thusly:

"A Chypre aroma with green, vetivert, woody, earthy, orris, minty, camphoraceous, cassis and grapefruit undertones and minty, camphoraceous, green, herbaceous, vetivert and galbanum topnotes".

EXAMPLE III

Preparation of a Cosmetic Powder Composition

Cosmetic powder compositions are prepared by mixing in a ball mill, 100 grams of talcum powder with 0.25% grams of each of the substances set forth in Table I below. Each of the cosmetic powder compositions has an excellent aroma as described in Table I below:

TABLE I

| Substance | Aroma Description |
|---|---|
| Compound having the structure: 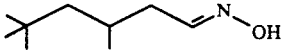 | A green, vetivert, woody earthy, orris, minty camphoraceous, cassis and grapefruit aroma with minty, camphoraceous, green, vetivert and galbanum topnotes. |
| Perfume composition of Example II. | A Chypre aroma with green, vetivert, woody, earthy, orris, minty, camphoraceous, cassis and grapefruit undertones and minty, camphoraceous, green, herbaceous, vetivert and galbanum topnotes. |

EXAMPLE IV

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table I of Example III are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aroma as set forth in Table I of Example III, the intensity increasing with greater concentrations of substance as set forth in Table I of Example III.

EXAMPLE V

Preparation of Colognes and Handkerchief Perfumes

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the and handkerchief perfumes at all levels indicated.

EXAMPLE VI

Preparation of Soap Compositions

One hundred grams of soap chips [per sample]-IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aroma as set forth in Table I of Example III.

EXAMPLE VII

Preparation of Solid Detergent Compositions

Detergents are prepared using the following ingredients according to Example III of Canadian Patent No. 1,007,948:

| Ingredients | Parts by Weight |
| --- | --- |
| "NEODOL ® 45-11 | 12 |
| (a $C_{14}$-$C_{15}$ alcohol ethoxylated with 11 moles of ethylene oxide) | |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example III at column 15 of U.S. Pat. No. 3,632,396, non-woven cloth substrates useful as dry-added fabric softening articles of manufacture are prepared wherein the substrate, the substrate coating and the outer coating and the perfuming material are as follows:
1. A water "dissolvable" paper ("Dissolvo Paper");
2. Adogen 448 (m.p. about 140° F.) as the substrate formulation (m.p. about 150° F.);
3. An outer coating having the following formulation (m.p. about 150° F.):
   57%—$C_{20-22}$ HAPS
   22%—isopropyl alcohol
   20%—antistatic agent
   1%—of one of the substances as set forth in Table I of Example III.

Fabric softening compositions prepared according to Example III at column 15 of U.S. Pat. No. 3,632,396 having aroma characteristics as set forth in Table I of Example III, consist of a substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example III.

EXAMPLE IX

Hair Spray Formulations

The following hair spray formulation is prepared by first dissolving PVP/VA E-735 copolymer manufactured by the GAF Corporation of 140 West 51st Street, New York, New York, in 91.62 grams of 95% food grade ethanol, 8.0 grams of the polymer is dissolved in the alcohol. The following ingredients are added to the PVP/VA alcoholic solution:

| Ingredients | Parts by Weight |
| --- | --- |
| Dioctyl sebacate | 0.05 |
| Benzyl alcohol | 0.10 |
| Dow Corning 473 fluid | 0.10 |
| (prepared by the Dow Corning Corporation) | |
| Tween 20 surfactant | 0.03 |
| (prepared by ICI America Corporation | |
| One of the perfumery substances as set forth in Table I of Example III. | 0.10 |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared with the Mona Industries Company) (3.0 weight percent) is melted with 2.0 weight percent coconut fatty acid (prepared by Procter & Gamble Company of Cincinnati, Ohio); 1.0 weight percent ethylene glycol disterate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUA ® 755N polymer (manufactured by GAF Corporation of 140 West 51st Street, New York, New York) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

What is claimed is:

1. The 3,5,5-trimethylhexanal oxime having the structure:

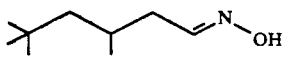

2. A process for augmenting or enhancing the aroma of a perfume composition, cologne or perfumed article comprising the step of adding to said perfume composition, cologne or perfumed article an aroma augmenting or enhancing quantity of the product defined according to claim 1.

3. A perfume composition comprising a perfume base and an aroma augmenting or enhancing quantity of the compound of claim 1.

4. A perfumed article comprising a perfumed article base and intimately admixed therewith an aroma augmenting or enhancing quantity of the compound defined according to claim 1.

5. A perfumed polymer comprising a polymeric base and intimately admixed therewith an aroma augmenting or enhancing quantity of the compound defined according to claim 1.

* * * * *